United States Patent [19]
Radunz et al.

[11] Patent Number: 5,508,390
[45] Date of Patent: Apr. 16, 1996

[54] DITERPENES HAVING IMMUNOMODULATORY ACTION

[75] Inventors: Hans-Eckart Radunz, Mühltal; Michael Wolf; Manfred Baumgarth, both of Darmstadt; Willy Kinzy, Gross-Rohrheim; Gerd-Albrecht Luckenbach, Darmstadt, all of Germany

[73] Assignee: Merck Patent Gesellschaft mit Beschrankter Haftung, Darmstadt, Germany

[21] Appl. No.: 655,582

[22] Filed: Feb. 15, 1991

[30] Foreign Application Priority Data

Feb. 17, 1990 [DE] Germany .................. 40 05 159.5

[51] Int. Cl.$^6$ .................. C07G 3/00; C07H 1/00; A01N 43/04; A61K 38/21
[52] U.S. Cl. .................. 536/4.1; 536/1.11; 536/123.1; 536/123.13; 424/85.5
[58] Field of Search .................. 536/4.1, 123, 1.11, 536/123.1, 123.13; 514/691, 2, 23, 25; 424/85.5, 195.1; 435/70.4; 544/1; 426/248

[56] References Cited

U.S. PATENT DOCUMENTS

| | | | |
|---|---|---|---|
| 4,351,346 | 9/1982 | Brummer et al. | 426/148 |
| 4,623,622 | 11/1986 | Anderson | 435/70.4 |
| 4,716,179 | 12/1987 | Hecker et al. | 514/691 |
| 4,840,934 | 6/1989 | Anderson | 514/2 |
| 4,843,067 | 6/1989 | Liu | 536/123 |
| 4,983,637 | 1/1991 | Herman | 514/724 |

OTHER PUBLICATIONS

Ahmed et al., "Labdane Diterpenes From Brickellia Vernicosa," Phytochemistry, vol. 25, No. 6, pp. 1385–1388, 1986.
Teresa et al., "Diterpenoids of Halimium Viscosum," Phytochemistry, vol. 24, No. 4, pp. 791–794, 1985.
Bohlmann et al., "Neue alpha–Santalen–Und Labdan–Derivate Aus Ayapana Amygdalina," Phytochemistry, vol. 18, pp. 1997–1998.

Hecker, "New Toxic, Irritant and Cocarcinogenic Diterpene Esters from Euphorbiaceae and from Thymelaecae," Pure and Appl. Chem., vol. 49, p. 1423.
Nair et al; Phytochemistry, vol. 15 (11), pp. 1776–1778 (1976).
Nair et al; Chemical Abstracts; 104(15): 126537q/Fitoterapia,(56)(4); 249–50;"Polyphenolic Compounds From Leaves of Acanthospermum hispidum".
De Pascual et al; Chemical Abstracts; 103(5);34870u;/Phytochemistry (24)(4), 791–4 "Diterpenoids of Halimium viscosum", 1985.

*Primary Examiner*—Douglas W. Robinson
*Assistant Examiner*—L. N. Leary
*Attorney, Agent, or Firm*—Millen, White, Zelano, & Branigan

[57] ABSTRACT

Diterpenes of the formula I

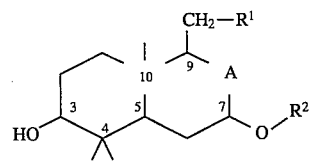

in which
$R^1$ is $-CH_2-C(CH_3)=CH-R^3$ or $-CH_2-CH(CH_3)-CH_2-R^3$,
$R^3$ is $-CH_2OH$, $-CHO$, $-COOH$ or $-COOR^4$,
$R^4$ is alkyl having 1 to 5 C atoms,
A is

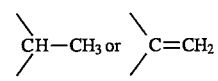

and
$R^2$ is H, pentoses, hexoses, di-/oligosaccharides or amino sugars,
are suitable for production of medicaments having immunomodulatory action, in particular stimulating T-cells.

6 Claims, No Drawings

DITERPENES HAVING IMMUNOMODULATORY ACTION

BACKGROUND OF THE INVENTION

The invention relates to diterpene derivatives which have an immunomodulatory action, in particular stimulating the T-cells, and are thus suitable as pharmaceutical active compounds.

The outbreak of diseases in the end means that the immune system of the individual concerned has been attacked and weakened in a certain way, at least temporarily. Apart from the very specific medicinal treatment of most diseases caused by specific infective agents, general strengthening of the immune defense has an important role, especially since it has been found that the development of tumors and of autoimmune diseases can be partly prevented or influenced in a positive way by generally-acting immunomodulatory substances. In the search for appropriate suitable substances, the pharmaceutical industry to an increasing extent uses, inter alia, various natural substances, mostly in the form of undefined extracts or essences. Known examples of these are the plant extracts from coneflower (*Echinacea*) or *Thuja*, which act as immunostimulants and are commercially available. All extracts of this type have the disadvantage that the actual active compounds as a rule are unknown and are additionally only present in very low concentrations, their isolation and the identification of the most complicated chemical structures cause not inconsiderable difficulties, the action is partly non-specific and is often a combination action, or the extract as such is toxic in numerous cases.

The object therefore existed of making available novel pharmaceutical active compounds which can be employed for strengthening the immune defense and which can be isolated from suitable natural plant substance preparations in an unambiguous manner, characterized and chemically modified so that a medicament which is well-defined in its properties, its structure and its pharmacological mode of action can be prepared.

SUMMARY OF THE INVENTION

It has now been found that certain diterpene derivatives, for example from plants of the genera *Acanthospermum, Brickellia, Halimium* or *Ayapana* and their variants, which have been chemically modified after isolation, have a surprisingly strongly pronounced immuno-modulatory action. A significant stimulation of T-cells, which play an important role in immune defense, is especially to be observed. The active compounds according to the invention are non-toxic within the dose range, do not have a mitogenic action on lymphocytes and also do not have a negative influence on the central nervous system. They are thus outstandingly suitable for use in immunotherapy.

The invention thus relates to pharmaceutical active compounds of the formula I

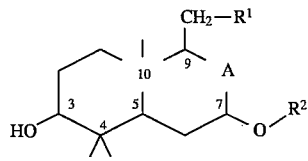

in which
$R^1$ is $—CH_2—C(CH_3)=CH—R^3$ or $—CH_2—CH(CH_3)—CH_2—R^3$,
$R^3$ is $—CH_2OH$, $—CHO$, $—COOH$ or $—COOR^4$,
$R^4$ is alkyl having 1 to 5 C atoms,
A is

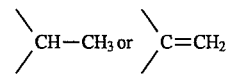

and
$R^2$ is H, pentoses, hexoses, a di-/oligosaccharides or amino sugars.

The invention relates in particular to the pharmaceutical active compound of the formula Ia

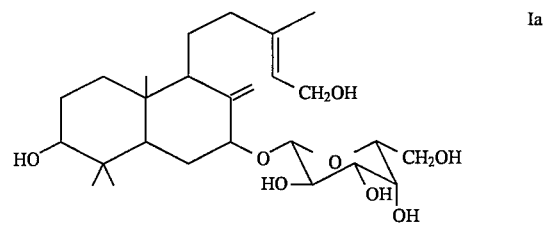

The invention further relates to a pharmaceutical preparation, which is characterized in that it contains at least one compound of the formula I and/or one of its physiologically acceptable acid addition salts.

The invention additionally relates to a process for the production of pharmaceutical preparations, characterized in that a compound of the formula I and/or one of its physiologically acceptable addition salts is brought into a suitable dose form together with at least one solid, liquid or semi-solid excipient or auxiliary.

The invention further relates to the novel compounds of the formula II

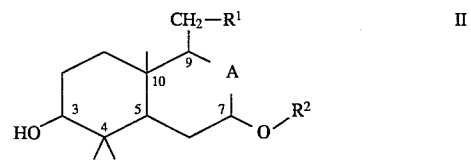

in which
$R^1$ is $—CH_2—C(CH_3)=CH—R^3$ or $—CH_2—CH(CH_3)—CH_2—R^3$,
$R^3$ is $—CH_2OH$, $—CHO$, $—COOH$ or $—COOR^4$,
$R^4$ is alkyl having 1 to 5 C atoms,
A is

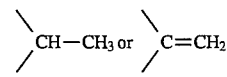

and
$R^2$ is penroses, hexoses, di-/oligosaccharides or amino sugars,
with the proviso that $R^1$ must not be $—CH_2—C(CH_3)=CH—CH_2OH$ or $—CH_2—C(CH_3)=CH—CHO$, A must not be

and $R^2$ must not be galactose at the same time.

The invention furthermore relates to a process for the preparation of the compounds of the formula II, characterized in that, alternatively, (a) the compound of the formula Ia is isolated from plants of the genus *Acanthosperum* and purified and at least one of the following synthesis steps is carried out:
   hydrogenation of the trisubstituted double bond,
   hydrogenation of the exocyclic double bond,
   oxidation of the —CH$_2$OH group of the diterpene component to the aldehyde or to the carboxylic acid, or to the carboxylic acid ester,
   substitution of the galactose residue by another sugar, (b) the compound of the formula III

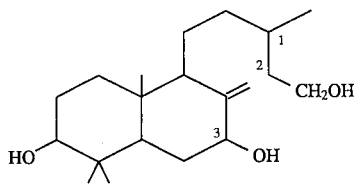

III is isolated from plants of the genera *Brickellia* or *Halimium* and purified and at least one of the following synthesis steps is carried out:
   dehydration of the C1–C2 bond in the formula III,
   hydrogenation of the exocyclic double bond,
   oxidation of the —CH$_2$OH group to the aldehyde or to the carboxylic acid, or to the carboxylic acid ester,
   glycosylation of the hydroxyl group on the C3 atom, or (c) the compound of the formula IV

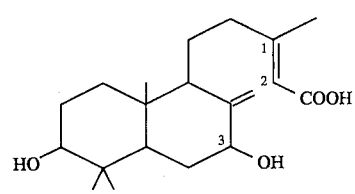

IV is isolated from plants of the genus *Ayapana* and purified and at least one of the following synthesis steps is carried out:
   hydrogenation of the trisubstituted double bond,
   hydrogenation of the exocyclic double bond,
   esterification of the carboxylic acid,
   reduction of the carboxylic acid or the carboxylic acid ester to the aldehyde or alcohol,
   glycosylation of the hydroxyl group on the C3 atom.

The invention finally relates to the use of the compounds of the formula I for the production of medicaments having immunomodulatory action, in particular stimulating T-cells.

By "immunomodulatory" is meant having a positive effect on the immune system by stimulating T-cell proliferation, including all known related effects and by activating T-lymphocytes.

The compounds of the formula I as such are known in some cases. The compounds of the formulae Ia, III and IV are known in particular. Their therapeutic action, on the other hand, is novel. The compounds of the formulae Ia, III and IV can be obtained, for example, in a known manner, from plants or parts of plants of the genera *Acanthospermum, Brickellia, Halimium* or *Ayapana*. They have been adequately characterized with respect to their structure (Nair et al. (1976), Phytochemistry 15, 1776; Bohlmann et al. (1979), Phytochemistry 18, 1997; de Pascual Teresa et al. (1985), Phytochemistry 24, 791; Achmed et al. (1986), Phytochemistry 25, 1385). The plants mentioned are plants which grow in the wild from tropical and subtropical zones, but also from temperate zones, such as, for example, South and Central America, India or Mediterranean areas. The isolation and purification of the compounds Ia, III and IV in the leaf or root segments is adequately described in the literature references mentioned.

Preferred species are: *Acanthospermum hispidum, Ayapana amygdalina, Halimium viscosum* and *Brickellia vernicosa.*

The novel compounds of the formula II, which also have an immunomodulatory or immunostimulating action, can be prepared, for example, in a manner known per se by standard methods of organic chemistry from the purified natural substances of the formulae Ia, III and IV.

Thus, for example, the trisubstituted double bond of the compounds of the formulae Ia, II and IV can be catalytically hydrogenated in a customary manner, but preferably with platinum in acetic acid.

The hydrogenation of the exocyclic double bond (A:

to give

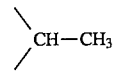

is preferably also carried out catalytically. Palladium on active carbon in methanol is particularly suitable here, but other catalysts can also be employed.

The oxidation of the allylic —CH$_2$OH groups, for example in the compounds of the formula Ia, II and III to give the corresponding allyl aldehydes is preferably carried out using active manganese dioxide in a manner known per se. If the allylic double bond is already hydrogenated, the oxidation of the primary alcohol on the diterpene radical to give the aldehyde can also be carried out with other oxidizing agents customary for this purpose, but preferably with copper, copper chromite or silver, since further oxidation to the carboxylic acid is inhibited in this case.

The oxidation of the primary alcohol or of the aldehyde concerned to give the carboxylic acid is carried out in a simple and known manner, for example using KMnO$_4$, CrO$_3$ or K$_2$Cr$_2$O$_7$ in pyridine.

The esterification of the —COOH radical with the alcohols of the type R$^4$OH is carried out, for example, by standard methods with acid or base catalysis. The desired radical R$^4$ can also be introduced by transesterifications.

The glycosylation of the C3 hydroxyl group of the compounds of the formulae III and IV or of the C7 hydroxyl group of the compounds of the formula I (R$^2$=H) is carried out by standard methods of carbohydrate chemistry. The sugar radical is preferably synthesized onto the diterpene building block by means of the Fischer, Helfrich or Koenigs-Knorr synthesis. α- and β-glycosides are formed in the reactions. By means of specific process variants, β-glycosides, for example, which are preferably prepared by the Koenigs-Knorr synthesis, are anomerized by treatment with, for example, titanium tetrachloride in apolar solvents and thus converted nearly quantitatively into the corresponding α-glycosides. Both the α- and the β-glycosides are suitable according to the invention. The sugar linkage can be carried out particularly advantageously using the imidate method (R. Schmidt (1986), Angewandte Chemie 98, 213).

To obtain the sugar-free active compounds according to the invention from the corresponding glycosylated compounds of the formulae I, Ia and II, for example, the glycoside is treated with, e.g., mineral acids, or preferably with an acidic ion exchanger, in a manner known per se.

An enzymatic cleavage with glycosidases, such as, for example, α,β-glucosidase or α,β-galactosidases, can also be carried out.

According to the invention, $R^2$ in the compounds of the formulae I and II is H, Pentoses, hexoses, di-/oligosaccharides or amino sugars. However, the corresponding glycosides are preferred, since, as a rule, they have the better active compound property in the sense of a T-cell stimulating action and, in particular in the case of mono-/disaccharides, have a better solubility. Among the sugars, the monosaccharides are preferred. Among these are, for example, pentoses such as ribose, threose or xylose, hexoses such as glucose, mannose, fructose or galactose or else, alternatively, amino sugars such as glucosamine or galactosamine. According to the invention, galactose is particularly preferred. Disaccharides which may be mentioned are, in particular, lactose, maltose or cellobiose. Examples of oligo- or polysaccharides are preferably raffinose or, alternatively, other tri- or tetrasaccharides. Starch or amylose are only of limited suitability because of their low solubility.

According to the invention, $R^1$ is $-CH_2-C(CH_3)=CH-R^3$ or $-CH_2-CH(CH_3)-CH_2-R^3$ in which $R^3$ is $-CH_2OH$, $-CHO$, $-COOH$ or $-COOR^4$. Particularly preferred $R^1$ radicals are $-CH_2-C(CH_3)=CH-CH_2OH$, $-CH_2-C(CH_3)=CH-CHO$, $-CH_2-C(CH_3)=CH-COOH$, $-CH_2-CH(CH_3)-CH_2CH_2OH$ and $-CH_2-CH(CH_3)-CH_2-COOH$.

In the ester $-COOR^4$, $R^4$ is preferably methyl, ethyl, n-propyl, n-butyl, iso-propyl, tert.-butyl or 2-methylpropyl.

The preferred meaning of A is

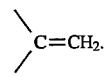

In the particularly preferred compounds of the formulae I and II $R^1$ is $-CH_2-C(CH_3)=CH-CH_2OH$ or $-CH_2-C(CH_3)=CH-CHO$, A is

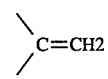

and $R^2$ is galactose, glucose, fructose or ribose, but in particular galactose.

The compounds according to the invention have several asymmetric C atoms in the diterpene moiety which cause a corresponding stereospecificity. Positions 3, 7, 9 and 10 of the compounds of the formulae I and II are particularly of importance in this case, since these are occasionally different in the various natural substance preparations. Thus, for example, in *Acanthospermum hispidum*, there is a 3R, 7R, 9S, 10R-configuration, in *Ayapana amygdaline* there is a 3R, 7R, 9R, 10S-configuration and in *Brickellia vernicosa* there is a 3S, 7R, 9S, 10R-configuration. Since the relative configuration on the centers of asymmetry concerned does not play an essential role in the pharmaceutical or therapeutic activity of the medicaments according to the invention mentioned, the configurations which the natural substances possess are preferred for reasons of easier availability. Of course, the corresponding compounds of the other configuration can be prepared according to the invention by chemically-caused isomerization according to standard methods.

A base of the formula I or II can be converted into the associated acid addition salt using an acid. Suitable acids for this reaction are in particular those which yield physiologically acceptable salts. Thus, inorganic acids can be used, for example sulfuric acid, nitric acid, hydrohalic acids such as hydrochloric acid or hydrobromic acid, phosphoric acids such as orthophosphoric acid, sulfaminic acid, in addition to organic acids, in particular aliphatic, alicyclic, araliphatic, aromatic or heterocyclic mono- or polybasic carboxylic acids, sulfonic or sulfuric acids, for example formic acid, acetic acid, propionic acid, pivalic acid, diethylacetic acid, malonic acid, succinic acid, pimelic acid, fumaric aid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxy-ethanesulfonic acid, benzenesulfonic acid, p-toluenesulfonic acid, naphthalene-mono- and -disulfonic acids and laurylsulfuric acid.

Conversely, acidic compounds of the formula I can be converted into one of their metal (for example Na, K or Ca) or ammonium salts by treating with a base.

Quaternary ammonium salts of the compounds of the formula I and II, for example in amino sugars, are obtainable by treating the latter with quaternizing agents, for example alkyl or aralkyl halides, sulfonates or sulfates such as methyl chloride, bromide, iodide, p-toluenesulfonate, dimethyl sulfate, ethyl bromide, benzyl chloride, expediently in the presence of an inert solvent, for example of an alcohol such as methanol or ethanol, at temperatures between −10° and +30° C.

The compounds of the formulae I, Ia and II according to the invention and their physiologically acceptable salts can be used for the production of pharmaceutical preparations by bringing them into a suitable dose form together with at least one excipient or auxiliary and, if desired, together with one or more other active compound(s). The preparations thus obtained can be employed as medicaments in human or veterinary medicine. Suitable carrier substances are organic or inorganic substances which are suitable for enteral (for example oral or rectal) or parenteral administration or for administration in the form of an inhalation spray and do not react with the novel compounds, for example water, vegetable oils, benzyl alcohols, polyethylene glycols, glycerol triacetate and other fatty acid glycerides, gelatin, soya bean lecithin, carbohydrates such as lactose or starch, magnesium stearate, talc and cellulose. Tablets, coated tablets, capsules, syrups, elixirs or drops are used for oral administration; coated tablets and capsules having gastric juice-resistant coatings or capsule shells are of especial interest. Suppositories are used for rectal administration, and solutions, preferably oily or aqueous solutions, but in addition suspensions, emulsions or implants are used for parenteral administration. Sprays which contain the active compound either dissolved or suspended in a propellant gas mixture (for example chlorofluorohydrocarbons) are used for administration as inhalation sprays. Expediently, the active compound is used in this case in micronized form, it being possible for one or more additional physiologically tolerable solvents to be present, for example, ethanol. Inhalation solutions can be administered with the aid of customary inhalers. The novel compounds can also be lyophilized and the lyophilizates obtained used, for example, for the production of injection preparations.

The preparations indicated can be sterilized and/or can contain auxiliaries such as preservatives, stabilizers and/or wetting agents, emulsifiers, salts for influencing the osmotic pressure, buffer substances, colorants and/or flavorings. If necessary, they can also contain one or more other active compounds, for example one or more vitamins.

Parenteral administration is preferred.

The immunomodulatory action of human or animal T-lymphocytes in vitro can be measured and determined, for example, in the following manner. The method is in the end based on the fact that T-cells are selectively stimulated to mitosis by means of the lectin phytohaemagglutinin (PHA), without a previous separation of other lymphocytes, such as, for example, macrophages or B-cells, being necessary. The strength of the T-cell activation in this case is dependent on the amount of PHA employed. If an approximately half-maximum activation of T-cells is chosen, the immunomodulation can be measured particularly well. Substances having an immunomodulatory activity which are added to the test batch increase (immunostimulation) or reduce (immunosuppression) the cell division already present. Without previous activation, however, therapeutically unsuitable substances cause an "undirected" cell division of the T-lymphocytes. This can lead to pathological reactions of the immune system. The incorporation of the measurement of the radioactive thymidine in newly synthesized DNA in the cells is used as an indirect measurement of cell division.

The active compounds according to the invention cause a significant stimulation of human T-lymphocytes. Thus, compared to the control value (without active compound), an increase in the T-cell activity of 30 to 80%, preferably of 40–65%, can be observed. The substances do not have a mitogenic active on lymphocytes.

The compounds and the pharmaceutical preparations of this invention can be administered to patients for whom modulation of their immune system would be beneficial. For example, suitable patients are those having either viral, bacterial or parasitic infections, e.g., influenza, herpes or hepatitis B; those having various cancers, such as leukemia, tumors or carcinomas, e.g., melanomas; and those needing support of vaccination responses and of desensitization of allergic reactions. Similarly, the compounds and pharmaceutical preparations of this invention can be administered prophylactically to patients who are not ill with immune-related diseases, but who stand an increased risk of becoming ill with diseases that are affected by the immune system as described above.

The glycosylated compounds generally show a higher activity than the non-glycosylated compounds. The substances are generally well tolerated. It was also not possible to show negative effects on the central nervous system. The substances according to the invention were preferably administered in doses of between about 0.1 mg and 10 mg, in particular between 0.5 mg and 2.5 mg per dose unit. The daily dose is preferably between 0.1 and 1 mg/kg of body weight. The dose for each specific patient depends, however, on various factors, for example on the activity of the specific compound employed, on the age, body weight, general state of health, sex, on the diet, on the excretion rate, on a possible active compound combination and on the severity of the respective disease to which the treatment applies. The compounds according to the invention are also best suited for prophylaxis.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 40 05 159.5, filed Feb. 17, 1990, are hereby incorporated by reference.

EXAMPLES

Example 1

Isolation of human lymphocytes from peripheral blood

Heparinized blood (10 units of lithium heparinate/ml of blood) from normal, healthy donors is diluted with the same volume of a suitable culture medium (RPMI 1640, GIBCO, KA). 10 ml of a suitable commercial gradient medium, i.e., (for example Lymphoprep®, Dr. Molter GmbH, FRA) in a 50 ml screw-closure tube are slowly covered with 20 ml of diluted blood. The gradient is centrifuged at 700×g for 20 minutes. 3 phases are formed during the course of this: the upper phase is aspirated and discarded. The sharp interphase containing the lymphocytes and monocytes/macrophages is then removed, transferred to a 15 ml screw-closure tube and made up to 14 ml with culture medium. The tube is centrifuged at 400×g for 15 minutes and the supernatant is decanted. 10 ml of culture medium are added to the tube again, and the cells are suspended and centrifuged at 275×g for 10 minutes. The supernatant is decanted, the pellet is broken up and taken up in 2 ml of culture medium, and the cells are suspended in this. A sample of 100 µl is removed from the suspension and diluted with a 1:10 Trypan blue solution (0.5%). The number of viable cells is determined in a Neubauer counting chamber. At least 100 cells are counted in at least 2 (opposite) quadrants.

Example 2

Mitogen stimulation

The lyphocytes isolated according to Example 1 are adjusted to $1\times10^6$ cells/ml of culture medium. 0.2 ml of cell suspension is employed per well of a microtiter plate having a flat bottom. The mitogen phytohaemagglutinin (PHA) is added to each of these microcultures so that about 0.04 µg of PHA/culture is present. The amount is chosen such that an approximately half-maximum T-cell activation is to be expected. Various concentrations (50–500 ng/culture) of the active compounds according to the invention were added to these batches. One batch is used as a control value.

Example 3

Proliferation of the lymphocytes

The microtiter plates containing the cultures according to Example 2 are cultured at 37° C. and 95% relative air humidity for 4 days in an incubator which is aerated with 10% $CO_2$. 18 hours before completion of the experiment, 0.5 µCi of $^3$H-thymidine/culture was added to the cultures. The cultures are then further incubated. On the 4th day, the cells are aspirated onto a glass fiber filter using a cell harvester.

The filter mat is added to a film, saturated with 10 ml of commercial scintillation fluid and then sealed in. The measurement of the radioactivity of $^3$H-thymidine incorporated into DNA is carried out in a commercial beta ray scintillation apparatus.

Example 4

Action of the compound of the formula Ia

The compound was isolated and purified by the method indicated by Nair et al. (Phytochemistry (1976), 15, 1776). In the test according to Examples 1 to 3, it shows a T-cell stimulating action of 51% and no mitogenicity for lymphocytes at a concentration between 100–200 mg/culture. In in vivo CNS screening (according to Irwin (1968), Psychopharmacologica 13, 222) in the mouse, no substance-related action can be determined after 1, 4 and 24 hours on administering 0.5 mg/kg (i.v.).

Example 5

Action of the compound of the formula Ia in which the allyl alcohol has been replaced by —CHO The compound was prepared analogously to Example 4 and investigated with respect to its immuno-stimulating action. Compared to the control value, an increase in activity (T-cells) of 40% was measured.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical preparation comprising an effective amount of a compound of formula I

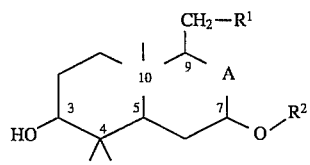

wherein $R^1$ is —$CH_2$—$C(CH_3)$=CH—$R^3$ or —$CH_2$—$CH(CH_3)$—$CH_2$—$R^3$, $R^3$ is —$CH_2OH$ or —CHO, A is

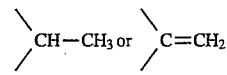

and $R^2$ is H, a pentose, a hexose or a disaccharide or a physiologically acceptable acid addition salt thereof, and a pharmaceutically acceptable excipient.

2. A pharmaceutical preparation of claim 1, wherein $R^2$ is a pentose, a hexose or a disaccharide.

3. A pharmaceutical preparation of claim 1, wherein the compound of formula I is the compound of formula Ia

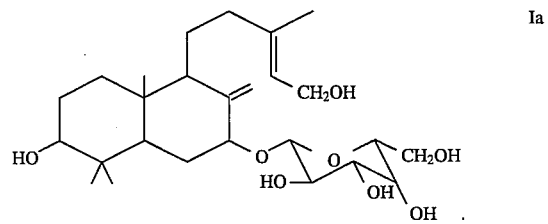

4. A method for modulating the immune system, comprising administering to a patient in need of such treatment an effective amount of a pharmaceutical preparation of claim 1.

5. A method of stimulating T-cell proliferation, comprising administering to a patient in need of such treatment an effective amount of a pharmaceutical preparation of claim 1.

6. A method of stimulating immune defense, comprising administering to a patient in need of such treatment an effective amount of a pharmaceutical preparation of claim 1.

* * * * *